United States Patent [19]

Barton

[11] 4,011,316
[45] Mar. 8, 1977

[54] CYCLOHEXA-2,5-DIENE-1-THIONES

[75] Inventor: Derek Harold Richard Barton, London, England

[73] Assignee: Research Institute for Medicine and Chemistry Inc., Cambridge, Mass.

[22] Filed: Feb. 24, 1975

[21] Appl. No.: 552,345

[52] U.S. Cl. .................... 424/241; 260/239.55 D; 260/397.2; 260/397.45; 260/397.5
[51] Int. Cl.² ........................................ A61K 31/58
[58] Field of Search ..... 260/239.57, 397.2, 397.45, 260/397.5

[56] References Cited

OTHER PUBLICATIONS

Bourdon, "Bull. Soc. Chem., France," 1958, pp. 722–725.
Kincle, "Berichte" 93, 1960, pp. 1043–1046.
Djerassi et al. "Jour. Org. Chem." vol. 26 (1961), pp. 4675–4677.

Primary Examiner—Elbert L. Roberts
Attorney, Agent, or Firm—Bacon & Thomas

[57] ABSTRACT

Compounds of the general formula

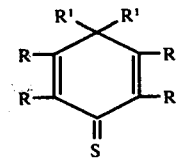

are provided wherein the substituents R, which may be the same or are different, represent hydrogen atoms or hydrocarbyl groups and the groups $R^1$ represent hydrocarbyl groups or adjacent pairs of substituents R, or R and $R^1$ together with the carbon atoms to which they are attached may constitute a non-aromatic ring structure, said hydrocarbyl groups or ring structure if desired carrying one or more substituents. Preferred compounds include steroid 1,4-diene-3-thiones of the cholestane, androstane, oestrane and pregnane series. Compositions containing these compounds are also provided.

22 Claims, No Drawings

CYCLOHEXA-2,5-DIENE-1-THIONES

This invention relates to cycloaliphatic thiones, in particular steroid thiones.

Compared with the aryl thiones, very few aliphatic thiones are known. Low molecular weight aliphatic thiones are known only to exist as trimeric species, i.e. 1,3,5-trithianes. Higher molecular weight aliphatic thiones do exist in monomeric form, but tautomerisation to the corresponding enethiol occurs to a major extent unless the structure renders it unlikely or impossible.

Steroid 1,4-diene-3-thiones would on theoretical grounds be considered to favour the enethiol form in view of the conjugation present but it has now been found however that, surprisingly, the cross-conjugated thione system found in a steroid 1,4-diene-3-thione or related compounds such as the thione analogue of santonin, exists in thione form as a stable entity.

The new compounds may be considered as cyclohexa-2,5-diene-1-thiones which may be substituted or form part of a polycyclic ring structure. However, in order to avoid isomerisation to tautomeric thiophenols, the 4-position of the cyclohexadiene ring should be disubstituted, i.e. should not carry a hydrogen atom. Such thiones can be represented, in general, by the formula

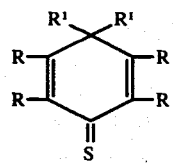

wherein the substituents R, which may be the same or different, represent hydrogen atoms or hydrocarbyl groups and the groups $R^1$ represent hydrocarbyl groups; or adjacent pairs of substituents R, or R and $R^1$ together with the carbon atoms to which they are attached may constitute a non-aromatic ring structure, said hydrocarbyl groups or ring structure if desired carrying one or more substituents. It is particularly preferred that one of the adjacent pairs of R and $R^1$ form part of a ring structure.

Where any of the groups R and $R^1$ are hydrocarbyl groups, these may, for example, be alkyl groups having 1-6 carbon atoms e.g. methyl groups as in santonin or in pregnanes. Where an adjacent pair $R^1$ and R represent a cyclic group, this maybe monocyclic or, as in steroids or in santonin, polycyclic. In both the latter cases, one group $R^1$ is alkyl while the other forms part of a ring structure. Such ring structures may be carbocyclic as in corticosteroids or may contain heterocyclic rings, e.g. the lactone ring in santonin.

The compounds of the invention may carry substituents, e.g. oxo or hydroxy groups, protected oxo or hydroxy groups such as acetal, ketal, ester or ether groups, carboxyl groups, esterified carboxyl groups, mercapto groups, halogen atoms, e.g. chlorine or fluorine atoms, or alkyl groups e.g. having 1-6 carbon atoms. Acetal or ketal groups may be cyclic or acyclic groups derived from mono or dihydric alcohols having 1-5 carbon atoms. Ester groups may be derived from aliphatic, araliphatic or aromatic carboxylic acids, preferably having 1-8 carbon atoms. Ether groups may be alkoxy, aralkoxy or aryloxy groups, preferably having 1-8 carbon atoms, or silyloxy groups, e.g. having three hydrocarbon substituents which may be alkyl, aralkyl or aryl groups, preferably having 1-8 carbon atoms.

These compounds may be prepared by any conventional procedure which is suitable, for example the treatment of an appropriate cyclohexa-2,5-dien-1-one with a reagent serving to replace an keto-group by a thione group. One such reagent is hydrogen sulphide and an acid, but this reagent is not ideally suited to compounds in the corticosteroid field because of acid catalyst dienone-phenol arrangement to the corresponding phenol or thiophenol, and because of sensitivity of the 17-side chain.

We have found that the treatment of a cyclohexa-2,5-diene-1-one with phosphorus pentasulphide or boron pentasulphide gives the corresponding thione in high yields. Any non-reactive solvent is appropriate for the reaction, for example tertiary amines such as triethylamine or pyridine; hydrocarbons such as alkanes, e.g. hexane, and light petroleum, or arenes e.g. benzene and toluene; ethers such as tetrahydrofuran and dioxan; nitriles such as acetonitrile and tertiary amides such as dialkyl formamides and acetamides. Tertiary amide solvents, however, react with the reagent, and are best used as co-solvents. Advantageously the solvent is a non-polar solvent, desirably an aryl hydrocarbon solvent, especially toluene.

The phosphorus or boron polysulphide must of course be used in a molecular ratio of at least 1:5 with the ketone substrate and preferably in excess, e.g. a ratio of 2:1 of more. The reaction is advantageously effected at a moderately elevated temperature, e.g. 60°–100° C.

Reactive groups in the substrate molecule, other than the keto group to be reacted must, of course, be protected. In particular, reactive hydroxyl or mercapto groups should be protected as esters, e.g. acetyl, benzoyl, or trifluoracetyl esters or ethers, e.g. methyl methylenedioxy or silyl ethers. In the steroids, 17,21-diol systems may be protected as 17,21-diacylates or 17,20:20,21-bismethylenedioxides. The relatively hindered steroid 11$\beta$-hydroxy group needs no protection from the polysulphide however, and keto groups other than the 3-keto react slowly with the reagent and thus may not need protection. Ester groups, amide groups and thioester groups are all less reactive than the ketones and thus similarly need no protection.

3-Thiones of steroid 1,4-dienes, possess interesting pharmacological activity of generally the same type as that of the parent 3-ones but characterised by particularly favourable assimilation into the body. Such steroids may be of the androstane, cholestane, oestrane or pregnane series. In particular, corticosteroid 3-thiones, especially when possessing an 11-oxygen function, e.g. a hydroxy or keto group, and a 17-oxygen function, e.g. a hydroxy or esterified hydroxy group, especially with a 17-aliphatic group as in the pregnane series, are noteworthy and the molecule should advantageously carry the typical corticoid 17,20,21 substituents, i.e. should be 20-deto-17,21-diols, mono- or diesters thereof, or ketalised derivatives such as acetonides and 17,20:20,21-bismethylenedioxy compounds. Other advantageous substituents include a 16$\alpha$- or $\beta$-methyl group, a 7-mercapto group and a 9$\alpha$-halo, especially fluoro, substituent.

Particular corticoid compounds of note according to the present invention include the 3-thione analogues of dexamethasone, betamethasone and prednisone and acetonides, bismethylenedioxy derivatives and 17- and/or 21- acylates thereof.

Other noteworthy steroid 1,4-diene-3-thiones according to the invention include aldosterone inhibitors such as the thione analogue of 1(2)-dehydrospironolactone, i.e. 17-hydroxy-7-mercapto-17α-pregna-1,4-diene-3-thione 21-carboxylic acid γ-lactone, 7-acetate.

Apart from their interesting pharmacological activity, the cyclohexa-2,5-diene-1-thiones are useful active intermediates in the preparation of other compounds. Oxidation with peracids such as m-chloroperbenzoic acid yields the corresponding 1-thione oxides (S-oxides) which comprise a further feature of this invention. The S-oxides are also surprisingly stable, but decompose when illuminated to form the corresponding 1-one. This facility of returning to the parent 1-one via the S-oxide makes the 1-thiones particularly useful intermediates in reaction sequences for which the 1-ones themselves are not well suited.

Thienol etherification may conveniently be achieved by treating the 1-thione with an enol-alkylating agent such as trialkyloxonium hexafluorophophate or tetrafluoroborate in an inert solvent such as a halogenated alkane, e.g. methylene chloride.

Thiones also react with 1,3-dipolar reagents to form heterocyclic derivatives. Thus, for example, reaction of a steriod-1,4-diene-3-thione with an aryl nitrile oxide, e.g. benzonitrile oxide yields a 3'-aryl-1', 4', 2'-oxathiazoline-5'-spiro-3-steroid. Thus, with prednisone BMD there is obtained 3'-phenyl-1', 4', 2'-oxathiazoline-5'-spiro-3-(17,20:20,21-bismethylenedioxypregna-1,4-dien-11-one). The aryl nitrile oxide may be prepared as described in Org. Synth. 49 by treatment of the appropriate α-chloro aldoxime with a tertiary amine such as triethylamine.

The androstane derivatives according to the invention e.g. 17-keto-, 17β-hydroxy- and 17β-hydroxy-17α-alkyl-androsta-1,4-dien-3-thiones have been found useful as anabolic agents and may advantageously be used to replace conventional agents. They have been found of particular use in the treatment of osteoporosis, whether sterile, post menopausal or steroid induced. A dosage of from 0.5 to 50 mg/day, preferably from 1.0 to 15 mg/day, is desirable.

The corticoid derivatives according to the invention, e.g. the 3-thione analogues of betamethasone, dexamethasone, prednisone, prednisolone, 16α- and 16β-methyl prednisolone and triamcinolone and their 17 and/or 21-esters and acetonides, have been found to be anti-inflmmatory agents which are longer acting than the corresponding ketones and have good topical activity with few side-effects. They may be used in low concentration topically for the treatment of e.g. rheumatoid arthritis and bursitis or may be administered orally or parenterally in dosages similar to the parent oxygenated steroids. In this manner they are especially suited to alternate day therapy.

The spironolactone compounds according to the invention are aldosterone antagonists and may be used alone or in combination with diuretics for the management of hypertension, congestive heart failure or chinosis. They may be administered at a rate of 10–1000 mg/day, preferably from 40–400 mg/day and are both orally active and good for alternate day therapy.

The S-oxide deratives of the above compounds are generally similar but are preferred for alternate day therapy. They may be used for both intramuscular and topical applications.

The compounds of the invention may be formulated in compositions using any of the conventional pharmaceutical carriers or excipients. The compounds may be administered parenterally in combination with an injectable liquid carrier such as sterile pyrogen-free water, sterile peroxide-free ethyl oleate, dehydrated alcohol, propylene glycol or a dehydrated alcohol/propylene glycol mixture. Such compositions may be injected intravenously, intramuscularly or intraperitoneally.

The compounds may be made up into orally administrable compositions containing one or more physiologically compatible carriers and/or excipients, and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. Tablets and capsules containing the new compounds may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats, emulsifying agents, for example lecithin, sorbitan monooleate or acacia; nonaqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

The compounds may also be administered topically. Such topical applications may, for example, be formulated in hydrophobic or hydrophilic bases as ointments, creams, lotions, paints and powders.

The invention will now be more particularly described in the following Examples which should not be interpreted as limiting the invention.

EXAMPLE 1

9α-Fluoro-16α-methyl-11,17,21-trihydroxypregna-1,4-diene-20-one-3-thione 17,20;20,21-bismethylene dioxide Dexamethasone-BMD (1.0g), phosphorus pentasulphide (150 mg) and pyridine (15 ml) were stirred at 90° C under argon for 1 hour. The solution was cooled, filtered and diluted with methylene chloride (100 ml). The purple solution was washed in turn with dilute hydrochloric acid (2 × 100 ml) and aqueous sodium bicarbonate, dried over MgSO$_4$ and evaporated to dryness. The residue was filtered through activated magnesium silicate in methylene chloride to give a purple product (290 mg) which was recrystallised from methylene chloride/hexane to yield the title product (dexamethasone BMD-3-thione), m.p. 212° C (dec.); $\delta 1.0$ (3H,d,J=6Hz,C-16 methyl protons); 1.2(3H,s,C-18 protons); 1.6(3H,s,C-19 protons); 4.0(2H,s,C-21 protons); 4.3 (1H,broad d,J=10Hz,C-11 proton); 4.9–5.3(4H,m,BMD protons); 6.9(1H, broad s,C-4 proton); 7.0(2H,s,C-1,2 protons); $\nu_{max}$ 3500 cm$^{-1}$, (m),(OH), 1630 cm$^{-1}$, (s),(C=C). $\lambda_{max}$ 331 nm ($\epsilon$17900), 580 nm ($\epsilon$25). Mass spectrum, M$^+$, 450. (Found C,63.84%; H, 6.66%; S, 7.27%. $C_{24}H_{31}FO_5S$ requires C, 63.97%; H, 6.94%, S, 7.18%).

Further elution of the column gave dexamethasone-BMD (205 mg).

EXAMPLE 2

9α-Fluoro-16β-methyl-11,17,21-trihydroxypregna-1,4-dien-20-one-3-thione 17,21-dipropionate Betamethasone 17,21-dipropionate (1.0 g), phosphorus pentasulfide (100 mg) and pyridine (15 ml) were stirred at 80° C for 45 minutes under atmosphere of argon. A further aliquot of phosphorus pentasulphide (100 mg) was then added and the mixture was stirred for another 90 minutes. The product (200 mg) was isolated in the same manner as described in Example 1 and recrystallised from methylene chloride/hexane to give blue plates of the title product (betamethasone 17,21-dipropionate-3-thione), m.p. 113° G; $\delta 1.0$ (s,C-18 protons); 1.6 (s,C-19 protons); 4.5 (1H,broad,G-11 protons); 4.5 (1H,broad,C-11 proton); 4.6 (2H,AB-q,J=16Hz, C-21 protons); 6.9 (1H,broad s, C-4 proton); 7.0 (2H,s, C-1,2 protons). $\nu_{max}$ 3570 cm$^{-1}$, (m), (OH), 1735 cm$^{-1}$, (vs), (C=O), 1635 cm$^{-1}$, (s),(C=C). $\lambda_{max}$ 330 nm ($\epsilon$19000), 575 nm ($\epsilon$24). Mass spectrum, M$^+$, 498. (Found: C, 64.74%; H, 7.19%; S, 6.02%. $C_{24}H_{31}FO_5S$ requires C, 64.59%, H, 7.16%; S, 6.16%.).

EXAMPLE 3

17,21-dihydroxypregna-1,4-dien-11,20dione-3-thione 17,20; 20,21-bismethylenedioxide Prednisone-BMD (4.0 g), phosphorus pentasulfide (4.0 g) and toluene (40 ml) were stirred at 70° C under argon for 4 hours. The solution was cooled, filtered and the residue was washed with toluene (15 ml). The filtrate was evaporated to low volume and chromatographed on activated magnesium silicate with methylene chloride. The fractions which were blue in colour were collected and evaporated to dryness to give a blue solid (3.0 g, 72%), which on recrystallisation from methylene chloride/hexane yielded the title product (prednisone-BMD-3-thione) m.p. 184°–187° C. $\delta 0.9$(3H,s,C-18 protons); 1.5(3H,s,C-19 protons); 4.0(2H,s,C-21 protons); 5.0–5.4(4H,m,BMD protons); 6.8–7.0(2H,m,C-2,4 protons); 7.5(1H,d,J=10Hz,C-1 proton). $\nu_{max}$ 1710 cm$^{-1}$, (s),(C=O), 1630 cm$^{-1}$, (s),(C=C). $\lambda_{max}$ 330 nm ($\epsilon$19500), 565 nm ($\epsilon$20). Mass spectrum, M$^+$, 416. (Found: C, 66.42%, H, 6.69%; S, 7.44%. $C_{23}H_{28}O_5S$ requires C, 66.32%; H, 6.78%; S, 7.70%.).

EXAMPLE 4

9α-Fluoro-16β-methyl-11,17,21-trihydroxypregna-1,4-dien-20-one-3-thione 17,21-dipropionate Betamethasone 17,21-dipropionate (2.3 g) in toluene (60 ml) with $P_2S_5$ (2.0 g) was stirred at 75°–80° C for 4 hours. The mixture was then cooled and filtered through an activated magnesium silicate CH$_2$Cl$_2$ column. Elution with further CH$_2$Cl$_2$ gave the 3-thione (1.45 g, 60%). By the foregoing procedure, the following compounds were also prepared:

17-keto androsta-1,4-diene-3-thione, m.pt 163°–5° C,

Found C 75.9, H 8.0, S 10.4, Calcd. C 76.0, H 8.1, S 10.7,

17β-hydroxyandrosta-1,4-diene-3-thione

17β-hydroxy-17α-alkyl androsta-1,4-diene-3-thione and the 17,21-diesters-3thiones of prednisone, prednisolone, 16α-methylprednisolone, 16β-methylprednisolone, dexamethasone, triamcinolone acetonide and other 17,21-diesters of betamethasone.

EXAMPLE 5

9α-Fluoro-16β-methyl-11,17-21-trihydroxypregna-1,4-dien-20-one-3-thione

The product of Example 4 (500 mg) in methanol (100 ml) was deoxygenated and stirred at 0° C under argon. N/10 NaOH (20 ml, 2 equiv.) was added and the solution was stirred at 0° C for 2 hours. Acetic acid (1 drop) was added and the mixture partitioned between CH$_2$Cl$_2$ and water. The organic layer was dried, evaporated to dryness and recrystallised from acetone/hexane to give blue microneedles m.pt. 170–4° C.

| Analysis: | Calc. | Found | |
|---|---|---|---|
| C | 64.68 | 64.72% | |
| H | 7.16 | 7.03% | |
| S | 7.85 | 7.38% | |
| PMR: | δ | H | Assignment H |
| | 1.1–1.3 | 6H (m) | C-16 and C-18 methyls |
| | 1.6 | 3H (S) | C-19 |
| | 4.2–4.5 | 3H(m) | C-21 and C-11 |
| | 6.7–7.2 | 3H(m) | vinyl |

IR: $\nu_{max}^{KBr}$ cm$^{-1}$: 3500 (vs). 1710 (m), 1640 (vs).

By the foregoing procedure were also prepared the 3-thiones of prednisone, prednisolone, 16α-methylprednisolone, 16β-methylprednisolone, and dexamethasone.

EXAMPLE 6

9α-Fluoro-16β-methyl-11,17,21-trihydroxypregna-1,4-dien-20-one-3-thione 17,21-dipropionate S-oxide The product of Example 4 (100 mg) in CH$_2$Cl$_2$ was stirred in the dark and m-chloroperbenzoic acid (50 mg) was added. The solution was washed with aqueous sodium bicarbonate, dried and evaporated to dryness. Recrystallization of the residue from CH$_2$Cl$_2$/hexane gave yellow crystals, m.pt. 110°–115° C.

| NMR: | δ | H | Assignment |
|---|---|---|---|
| | 1.0–1.4 | multiple methyl resonances | C-18, C-16 and ester |
| | 1.6 | 3H (s) | C-19 |
| | 4.55 | 2H (AB quart.) | C-21 protons |
| | 6.2–7.3 | 3H (m) | vinyl protons |

IR: $\nu_{max}^{KBr}$ 3500 (m.) 1730 (vs.) 1190 (vs) cm$^{-1}$.

| Analysis | Found | C,62.42; H, 7.21; S, 5.81 % |
|---|---|---|
| | Reg | C,62.66; H, 6.95; S, 5.98 % |

By the foregoing procedure, the S-oxides of the 3-thiones of 17,21-diesters of prednisone, prednisolone, 16α-methylprednisolone, 16β-methylprednisolone and dexamethasone and of triamcinolone acetonide were also prepared.

EXAMPLE 7

9α-Fluoro-16β-methyl-11,12-21-trihydroxypredgna-1,4-dien-20-one-3-thione S-oxide The procedure and scale of Example 6 was used to prepare the title product from the product of Example 5. Recrystallization from ethyl acetate/hexane gave yellow crystals m.pt. 170°–4° C.

| PMR: | δ | H | Assignment H |
|---|---|---|---|
| | 1.1 | 3H (d)J=7Hz) | C-16 methyl |
| | 1.1 | 3H (s) | C-18 |
| | 1.6 | 3H (s) | C-19 |
| | 4.0 | 3H (bm) | OH |
| | 4.4 | 2H (AB quartet) | C-21 |
| | 4.4 | 1H (bm) | C-11 |
| | 6.5–7.1 | 3H (m) | vinyl |

IR: $\nu_{max}^{KBr}$ cm$^{-1}$ 3500 (vs), 1110(m).

Analysis Found
C,61,85;
H,6,97;
Reg
C,62,24;H,6,
89;S,7,55%

By the foregoing procedure, the S-oxides of the 3-thiones of prednisone, prednisolone, 16α-methylprednisolone, 16β-methylprednisolone, and dexamethasone were also prepared.

EXAMPLE 8

3'-phenyl-1', 4', 2', -oxathiazoline-5'-spiro-3-(17,20:20,21-bismethylenedioxypregna-1,4-dien-11-one The product of Example 3 (416 mg) and PhCCl=NOH (400 mg) in dry benzene (10 ml) were treated with anhydrous triethylamine (1 ml). The residue after evaporation was passed through activated magnesium silicate and the product was eluted with 70% CH$_2$Cl$_2$ in hexane.

Recrystallization from CH$_2$Cl$_2$/hexane gave colorless plates m.pt. 134 C UV:$\lambda_{max}$. 246nm (20000), 300 nm (1700). IR:$\nu_{max}$. KB$\nu$ cm$^{-1}$: 1700 (vs), 1660 (w).

| PMR: | δ | H | Assignment H |
|---|---|---|---|
| | 0.9 | 3H (s) | C-18 |
| | 1.4 | 3H (two peaks) | C-19 |
| | 4.0 | 2H (s) | C-21 |
| | 4.S–S.1 | 4H (m) | BMD |
| | 0.0–7.0 | 3H (m) | vinyl |
| | 7.3–7.7 | 5H (m) | aryl |

EXAMPLE 9

3-Ethoxy-17,21-dihydroxypregna-1,3,5-triene-11,20-dione 17,20:20,21-bismethylene dioxide Prednisone BMD 3 thione (from Example 3) (1.0 g) in dry CH$_2$Cl$_2$ (25 ml) over 4A molecular sieve and under an atmosphere of argon, was treated with 1 equiv. (2.5 ml) of triethyloxonium tetrafluoroborate in CH$_2$Cl$_2$ solution. The mixture was stirred for 2.5 hrs. and then quenched with 1.4 equiv. (643 mg) of 1,8-bis-(dimethylamino)naphthalene. The solution was filtered to remove sieves and amine tetrafluoroborate and the filtrate applied to 9, 20cm × 20 cm preparative chromatography plates. The band corresponding to the desired product was removed from each plate and extracted with CH$_2$Cl$_2$. The extracts on evaporation gave 0.38 g of product; recrystallization ex hexane/CH$_2$Cl$_2$ gave off white crystals, m.p. 178°–180° C.

| PMR: | δ | H | Assignment |
|---|---|---|---|
| | 0.8 | 3(s) | C-18 |
| | 1.25 | 3(t, J=7Hz) | CH$_3$-CH$_2$-S |
| | 1.30 | 3(s) | C-19 |
| | 2.75 | 2(q, J=7Hz) | CH$_3$-CH$_2$-S |
| | 4.0 | 2(s) | C-21 |
| | 5.0–5.2 | 4(m) | BMD-methylenes |
| | 5.3–5.8 | 3(m) | C-2,4,6 |
| | 6.45 | 1(d,J=10Hz) | C-1 |

IR: (KBr) 2950 (m), 1700 (s), 1100 (s), 1080 (s), 945 (s), 745 (m) cm$^{-1}$ [a]$_D$ = −216° C (c=1.20, CH$_2$Cl$_2$).

UV λ$_{max}^{CH_3CN}$ = 326 nm (ε = 6400)

EXAMPLE 10

Preparation of 17-hydroxy-7-mercapto-17α-pregna-1,4-diene-3-thione-21-carboxylic acid γ-lactone, 7-acetate To 17-hydroxy-7-mercapto-3-oxo-17α-pregn-1,4-diene-21-carboxylic acid γ-lactone, 7-acetate (207 mg, 0.5 m. moles) in toluene (6 ml), was added phosphorus pentasulfide (200 mg, 0.9 m moles) in a flask fitted with a reflux condenser and a gas inlet tube. The mixture under an argon atmosphere, was heated to 70°±5° with constant stirring until t.l.c. revealed the onset of formation of undesired by-products (4 hrs.).

The mixture was filtered, the insoluble material being washed with methylene chloride and directly applied to an activated magnesium silicate column. Elution with methylene chloride gave the product as a dark blue glass after solvent removal under vacuum. The crude product was recrystallized from acetone/hexane to yield 90 mg of pure thione as deep blue micro needles (m.p. >240°, loss of color and dec.).

UV: λ$_{max}$. :330mμ (ε = 24,700)in MeOH

Ir: $\nu_{max}^{KBr}$ cm$^{-1}$: 3000 (m), 1775 (vs), 1690 (s), 1630 (s), 1180(s), 1135 (s), 1025 (m), 805 (m).

| PMR: | δ | H | Assignment H |
|---|---|---|---|
| | 1.0 | 3 (s) | C-18 |
| | 1.3 | 3 (s) | C-19 |
| | 2.35 | 3 (s) | —S—C—Me ‖ O |
| | 4.0 | 1 (m) | C-1 |
| | 7.5 | 2 (m) | C-2, C-4 |

EXAMPLE 11

Reaction of Santonin with P$_2$S$_5$/toluene

Santonin (2.0 g) and P$_2$S$_5$ (3 g) in toluene (40 ml) were stirred at 70° C for 4 hrs. The reaction was then found to be about 50% complete and the t.l.c. showed that the less polar product was blue in color. Further reaction resulted some decomposition products forming. Isolation of the blue fraction on activated magnesium silicate gave a blue crystalline solid. mp 143°–144°

Analysis: Found C,68.87; H, 6.95; S, 12.22%.
Reg C, 68.67; H, 6.91; S, 12.22%.

EXAMPLE 12

Pharmaceutical Compositions

Compositions containing the various classes of compounds of the invention may be formulated as follows:
a. 12.5 or 0.5 androstane steroid
  8g methyl sterate
  up to 200g lactose
The mixture is pressed after mixing and 1000 tablets are prepared. A suitable dose could be from 1–4 per day
b. 10g or 100g or 250g spironolactone steroid
  5g methyl stearate
  up to 500g lactose
The mixture may be pressed to provide 1000 tablets, with a suitable dose rate of 1–4 per day.
c. 0.3 or 0.8g betamethasone derivative
  or 3 or 7g prednisolone derivative
  8g methyl stearate
  up to 250g lactose
The mixture may be pressed to yield 1000 tablets, with a suitable dose rate of 1–4 per day or 1–4 on alternate days.

EXAMPLE 13

Compositions for topical application a. For the preparation of an ointment are throughly mixed

| | |
|---|---|
| 30g propylene glycol monostearate | |
| 30g sorbitol monostearate | |
| 0.5g 4-chloro m-cresol or methyl paraben. | |
| Add polyethylene glycol/propylene glycol to 1 kg. | |
| Into this ointment are stirred | |
| betamethasone derivative | 1g or 2g |
| or betamethasone dipropionate derivative | 0.5g or 1g |
| or prednisolone derivative | 2g or 5g |

The ointment is applied to the affected area 1–4 times daily. The area under treatment may, in the case of arthritis or bursitis, be covered with a plastic film and sealed at the edges with adhesive.
b. For the preparation of a cream The cream may be prepared in the same manner as the ointment, except that the polyethylene glycol/polypropylene glycol are replaced by a mixture of liquid and white petrolatum containing hydrogenated lanolin.

I claim:

1. A compound of the general formula wherein the substituents R, which may be the same or different, represent hydrogen atoms or alkyl groups of 1–6 carbon atoms and the groups $R^1$ represent alkyl groups of 1–6 carbon atoms or an adjacent pair of substituents R and $R^1$ together with the carbon atoms to which they are attached form part of the ring structure of a steroid 1,4-diene-3-thione of the cholestane, androstane, oestrane or pregnane series or of santonin 3-thione; or an S-oxide of said compound.

2. A compound as claimed in claim 1 which is a steroid 1,4-diene-3-thione of the cholestane, androstane, oestrane or pregnane series.

3. A compound as claimed in claim 2 carrying at least one substituent selected from the group consisting of a 7-mercapto or 7-($C_1$–$C_8$) carboxylic acylthio group, a 9α-halogen atom, an 11-hydroxy or 11-keto group, a 16-methyl or 16-hydroxy group, a 17-hydroxy or 17-($C_1$–$C_8$) carboxylic acyloxy group, a 21-hydroxy or 21-($C_1$–$C_8$) carboxylic acyloxy group, a 17,20:20,21-bismethylenedioxy group, a 16,17-acetonide grouping and a 17-hydroxy-21-carboxy-17,21-lactone grouping.

4. A compound as claimed in claim 3 which is a 17,21-dihydroxy-20-keto-pregna-1,4-diene-3-thione.

5. A compound as claimed in claim 2 which is a 3-desoxy-3-thione of dexamethasone, betamethasone, or prednisone.

6. A compound as claimed in claim 4 which is the 3-desoxy-3-thione-17,21-dipropionate of dexamethasone, betamethasone, or prednisone.

7. The compound of claim 6 which is 9α-fluoro-16β-11,17,21-trihydroxypregna-1,4-dien-20-one-3-thione 17,21-dipropionate.

8. The 3-desoxy-3-thione of 1(2)-dehydrospironolactone.

9. An S-oxide of a compound as claimed in claim 1.

10. A process for the preparation of a compound as claimed in claim 1 in which the corresponding cyclohexa-2,5-dien-1-one is reacted with phosphorus pentasulphide or boron pentasulphide.

11. A process as claimed in claim 10 in which the cyclohexa-2,5-dien-1-one is reacted with phosphorus pentasulphide.

12. A process as claimed in claim 11 in which the ration of phosphorus pentasulphide to ketone is at least 1:5.

13. A process as claimed in claim 12 in which said ratio is 2:1 or more.

14. A process as claimed in claim 11 in which the reaction temperature is 60°–100° C.

15. A process as claimed in claim 10 in which the cyclohexa-2,5-dien-1-one is reacted with boron pentasulphide.

16. A process as claimed in claim 10 in which the thione formed is subsequently oxidised to the corresponding S-oxide.

17. A process as claimed in claim 10 in which the thione formed is reacted with an enol-alkylating agent to form the corresponding thienol ether.

18. A process as claimed in claim 10 in which the thione formed is reacted with an aryl nitrile oxide to form a 3-aryl-1,4,2-oxathiazoline-5-spiro-grouping.

19. A pharmaceutical composition containing at least one compound as claimed in claim 4 in conjunction with a pharmaceutical carrier or excipient.

20. A pharmaceutical composition containing the compound of claim 8 in conjunction with a pharmaceutical carrier or excipient.

21. A method of combatting inflammatory conditions in animals and humans wherein an effective dose of a compound as claimed in claim 4 is administered orally, parenterally or topically to a subject suffuring from said condition.

22. A method of combatting rheumatoid arthritis and bursitis in humans wherein effective dose of a compound as claimed in claim 4 is administered topically to a subject suffering from said condition.

* * * * *